(12) United States Patent
Hsu et al.

(10) Patent No.: US 6,403,357 B1
(45) Date of Patent: Jun. 11, 2002

(54) THERMOSTABLE D-HYDANTOINASE AND THE APPLICATION THEREOF

(75) Inventors: Wen-Hwei Hsu, Taichung; Chao-Hung Kao, Taipei, both of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/836,992

(22) Filed: Apr. 18, 2001

(30) Foreign Application Priority Data

Aug. 24, 2000 (TW) ........................................ 089117053

(51) Int. Cl.[7] .............................. C12N 9/86; C12N 15/55
(52) U.S. Cl. .................... 435/231; 435/320.1; 536/23.2
(58) Field of Search .............................. 435/231, 320.1; 536/23.2

(56) References Cited

U.S. PATENT DOCUMENTS

| | | | |
|---|---|---|---|
| 4,912,044 A | 3/1990 | Jacob et al. | 435/172.3 |
| 5,523,224 A | 6/1996 | Burtscher et al. | 435/231 |
| 5,679,571 A | 10/1997 | Burtscher et al. | 435/325 |

OTHER PUBLICATIONS

Luska, V., et al. (1997) Apl. Biochem. Biotech. 62, 219–231.*

R. Oliviera, E. Fascetti, L. Angelini and L. Degan. *Microbial Transformation of Racemic Hydantions to $_D$–Amino Acids*, Biotechnology and Bioengineering, vol. XXIII, 1981, pp. 2173–2183.

* cited by examiner

*Primary Examiner*—Charles L. Patterson, Jr.
(74) *Attorney, Agent, or Firm*—Fish & Richardson P.C.

(57) ABSTRACT

The invention discloses a novel thermostable D-hydantoinase, and relates to the nucleic acid sequence, amino acid sequence and vector constructs of the enzyme. The thermostable D-hydantoinase of the invention shows about 45%–70% identity in amino acid sequence with other D-hydantoinases. The thermostable D-hydantoinase of the invention converts 5'-substituted D-hydantoinase to the corresponding N-carbamoyl-D- and/or -L-$\alpha$/$\beta$-amino acids, and retains at least 50% activity after 30 days at 50° C. In addition, the enzyme activity can also enhanced by certain divalent cations.

12 Claims, 13 Drawing Sheets

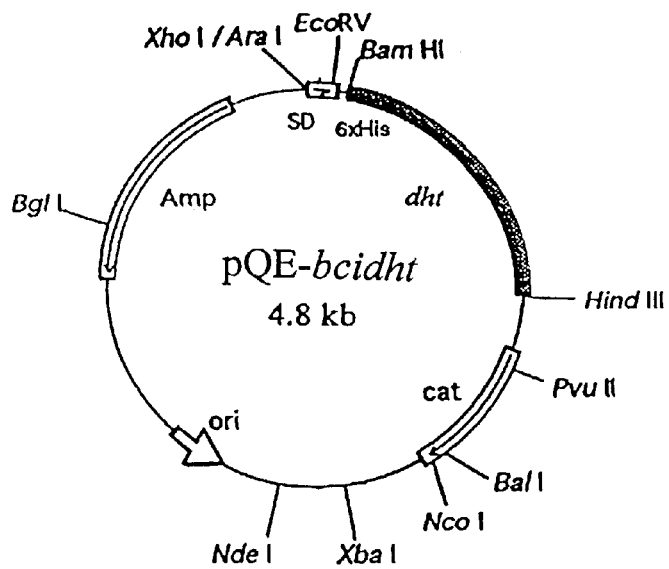
(A)
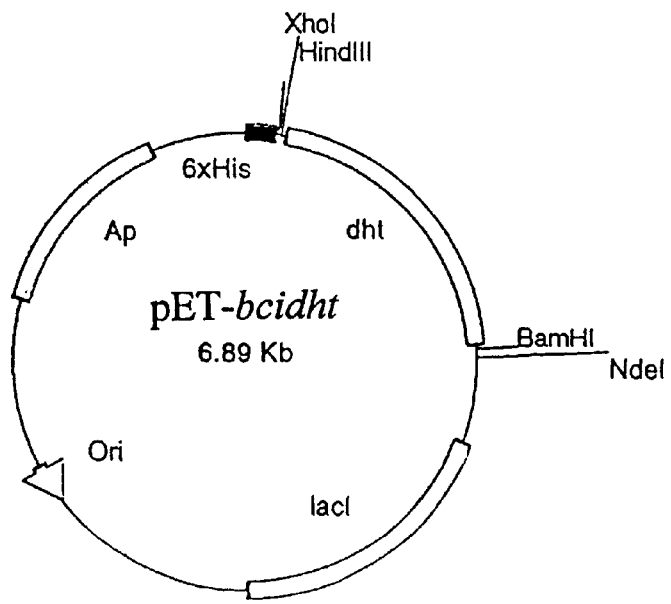
(B)
FIG. 3 aacctgtatcaactgcaacaaatgccatatcgcctgtgaggacacttcgcaccaatgcat 60
tgatatcgtcaaggacgccgcaacgggaaaagagcggttggtagtgcgcgaggaagactg 120
cgtcggctgcaacctgtgctcgattgtctgtccggtggaaggaacgatcgagatggtgga 180
gattccgacgggcaagccgccgctttcctggaaccagcgccaggctgctttggcaggcgg 240
gggcagttgcgagacgtaagttctagggccgatggcatgaatggggcgcaagcggcatag 300
catgtacgaggaacgggatgtctcatttatgcacggcaggggaaaggagcgaggaaggtc 360
atgaaaaaatggattcgcaacgggacggttgtgacggcgtcagacacgtatcaggcagac 420
  M  K  K  W  I  R  N  G  T  V  V  T  A  S  D  T  Y  Q  A  D
gtgctgatcgacggcgaaaaagtcgtcgcgatcggctcggacctgcaagcaacagatgcg 480
  V  L  I  D  G  E  K  V  V  A  I  G  S  D  L  Q  A  T  D  A
gaggttatcgacgcaaccgggtactatttgcttccgggcggcattgatccgcacacgcac 540
  E  V  I  D  A  T  G  Y  Y  L  L  P  G  G  I  D  P  H  T  H
ctcgacatgccgtttggcggcacggttacatccgataacttttcacgggcacaaaagcc 600
  L  D  M  P  F  G  G  T  V  T  S  D  N  F  F  T  G  T  K  A
gccgcattcggcgggacgacgagcatcgtggacttttgcctgacgagcaaaggggagtcg 660
  A  A  F  G  G  T  T  S  I  V  D  F  C  L  T  S  K  G  E  S
ctccactccgcgattgcgacctggcacgaaaaagcgaggggcaaagccgtcatcgactac 720
  L  H  S  A  I  A  T  W  H  E  K  A  R  G  K  A  V  I  D  Y
ggcttccacctgatggtgtccgatgccaacgaccatgtgctggaagagctggagtcggtc 780
  G  F  H  L  M  V  S  D  A  N  D  H  V  L  E  E  L  E  S  V
gtgaacaacgaaggcattacttcactcaaagtgttcatggcgtacaaaaacgtgctgatg 840
  V  N  N  E  G  I  T  S  L  K  V  F  M  A  Y  K  N  V  L  M
gccgacgacgaaactttgttcaagacgctgatccgcgccaaggagctaggggcgttggtc 900
  A  D  D  E  T  L  F  K  T  L  I  R  A  K  E  L  G  A  L  V
caagtgcacgccgagaacggggacgtgctcgattatttgaccaagcaggcgctggccgaa 960
  Q  V  H  A  E  N  G  D  V  L  D  Y  L  T  K  Q  A  L  A  E
ggaaataccgatccgatctaccacgcctacacccgtccgccggaagcggagggagaggcg 1020
  G  N  T  D  P  I  Y  H  A  Y  T  R  P  P  E  A  E  G  E  A
acaggccgcgcgattgcgctcacggcgctcgcggatgcccagttgtacgtcgtgcacgtg 1080
  T  G  R  A  I  A  L  T  A  L  A  D  A  Q  L  Y  V  V  H  V
tcctgcgccgacgccgttcgccggatcgccgaggcgcgcgaaaaaggctggaacgtctac 1140
  S  C  A  D  A  V  R  R  I  A  E  A  R  E  K  G  W  N  V  Y
ggagaaacatgtccgcaatatttggtgctcgatatcaccgcgctggaaaagccggacttc 1200
  G  E  T  C  P  Q  Y  L  V  L  D  I  T  A  L  E  K  P  D  F
gaaggggcgaaatacgtctggtccccgccgctgcgggaaaagtggaaccaggacgtactg 1260
  E  G  A  K  Y  V  W  S  P  P  L  R  E  K  W  N  Q  D  V  L

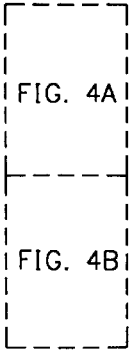

FIG. 4A

```
tggagcgcgctgaaaaacgggattttgcaaacagttggttccgaccactgtccgttcaac 1340
 W  S  A  L  K  N  G  I  L  Q  T  V  G  S  D  H  C  P  F  N
ttttccgggcaaaaagagctgggccgcagagatttacgaaaattccgaatggcggcccg 1400
 F  S  G  Q  K  E  L  G  R  R  D  F  T  K  I  P  N  G  G  P
atcattgaggatcgcatgaccatcctctttttccgagggcgtgcgcaaaggcaaaatcagc 1460
 I  I  E  D  R  M  T  I  L  F  S  E  G  V  R  K  G  K  I  S
ctgaatcaattcgtggacatcacctccaccaaagtcgccaagctgtttggcatgttcccg 1520
 L  N  Q  F  V  D  I  T  S  T  K  V  A  K  L  F  G  M  F  P
caaaaaggcacgattgcggttggctccgatgcggacatcgtcttgttcgacccgactgtg 1580
 Q  K  G  T  I  A  V  G  S  D  A  D  I  V  L  F  D  P  T  V
cagcggacgatttcggtggagacgcaccatatgaatgtggactacaacccgtttgaaggc 1640
 Q  R  T  I  S  V  E  T  H  H  M  N  V  D  Y  N  P  F  E  G
atgcaggttcacggcgacgtcatttctgtgctttcccgcggcgcgttcgtcgtccgcaac 1700
 M  Q  V  H  G  D  V  I  S  V  L  S  R  G  A  F  V  V  R  N
aagcagttcgtcggccatgcgggggcgggccgctacgtgaagcggtcgacgtttgccaga 1760
 K  Q  F  V  G  H  A  G  A  G  R  Y  V  K  R  S  T  F  A  R
ccatagccaaatgcaaatgctggggtgaggaggagcaagatggcggataaagtgacgatc 1840
 P  *
gggctgattcaggccaaaaatgacgtgcacggcgacgagccggttcatcttcacaaggaa 1900
aaggcgatcgaaaagcatgtgaaaatggtgcgggaggctgctggcaaaggggcgcagatc 1960
atctgtctgcaagaaatttttacggcccttattttgcgcggagcaaagcacgaaatgg 2020
tacgaagcggcggaagaggtgccgaacggcccgactgtgcagcagttttccgcgctgggc 2080
aaggagctcgggaccgtgctgatcttgcccgtgtatgaaaaggtcggcatcggcacctac 2140
```

FIG. 4B

THERMOSTABLE D-HYDANTOINASE AND THE APPLICATION THEREOF

BACKGROUND OF THE INVENTION

1. Field of the Invention

The present invention relates to a novel thermostable D-hydantoinase, and particularly to the nucleic acid sequence, amino acid sequence, vector constructs and the application thereof.

2. Description of the Related Arts

D-amino acids are usually called unnatural amino acids. They are not used as frequently as L-amino acids, but are becoming more and more important, especially in the field of pharmacy, e.g. in the preparation of penicillin, cephalosporin and β-lactam antibiotic precursors.

Amoxicillin can be obtained by reacting D-p-Hydroxyphenylglycine (D-p-HPG) with 6-aminopenicillianic acid. Recently, the market for amoxicillin has expanded and grown more than 12% with each year. Due to the enhanced sales volume of the products, the demands for D-p-HPG precursors have increased markedly, with growth over 10% each year.

D-p-HPG was once chemically synthesized from D,L-p-hydroxyphenylhydantoin (D,L-p-HPH). However, this method has numerous disadvantages, including: (1) many reaction steps are required; (2) expensive solvents are employed; (3) products with low optical purity are obtained; (4) low yield is obtained in each reaction cycle; (5) complex steps are required for separation of racemizing residues; and (6) environmental contamination is induced during chemical processes (Takahashi et al., 1979, *J. Ferment. Tech.* 57:328–332). Yamada et al. (1978, *J. Ferment. Tech.* 56:484–491) developed a new process for the production of D-amino acids by unsymmetrical transformation of D,L-5'-substituted hydantoin with the D-hydantoinase in microorganisms, followed by treatment with nitrous acid. The products obtained by such chemo-enzymatic process are more economical and convenient. In addition, no measure to ensure optical purity are taken during this process.

Although the chemo-enzymatic process solves the problem in purity in the optical compound, many steps are still required, thereby increasing production costs. In addition, the reaction temperature has to be brought to below 20° C. when the step of chemical decarbamoylation is carried out, otherwise D-p-HPG will be further hydrolyzed into 4-hydrobenzaldehyde. For a more convenient production method, many studies have become involved in searching for a microorganism capable of directly hydrolyzing substrates into D-amino acids. Olivieri et al. (1979, *Enzyme Microb. Tech.* 1:201–204) found that the crude extracts of *Agrobacterium radiobater* NRRL B 11291 possess the activity of N-carbamoyl-D-amino acid amidohydrolase, which can further hydrolyze N-carbamoyl-D-amino acid into D-amino acid. Therefore, the D-amino acids can be produced using D-hydantoinase and N-carbamoyl-D-amino acid amidohydrolase in microorganisms (Olivieri et al. 1981, *Biotech. Bioeng.* 23:2173–2183). Only one step is required in this method, and the racemizing residues can be completely converted to D-amino acids.

D-hydantoinase (EC 3.5.2.2) is useful in the production of N-carbamoyl-D-amino acids. Currently, microorganisms in which the D-hydantoinase gene has been cloned include *Agrobacterium radiobater, Agrobacterium tumefaciens, Bacillus stearothermophilus, Bacillus thermoglucosidasius, Pseudomonas putida* DSM 84, etc. The peptide length of D-hydantoinase ranges between 460 and 510 residues.

The two-step enzymatic process is desired for the production of D-amino acids in industries, thereby realizing cost savings for the manufacture. However, the current difficulty is the poor solubility of D,L-p-HPH. To overcome this problem, the reaction temperature has to be elevated to 50° C. to increase the solubility. In the current cloned D-hydantoinases, however, there is a loss of or decrease in activity at this temperature. Only a few D-hydantoinases cloned from thermophilic Bacillus carry sufficient heat-resistance. See, for example, U.S. Pat. Nos. 5,523,224, 5,679,571, and 4,912,044. The microorganisms in which the heat-resistant D-hydantoinase has now been cloned include *Bacillus stearothermophilus*, and *Bacillus thermoglucosidasius*. However, some problems in stability and efficiency still exist in these enzymes when they are applied in the industrial process.

Therefore, there is still a need for a thermostable D-hydantoinase, in which the enzyme can maintain activities under high temperature (e.g. 50° C.), and perform a preferred catalytic reaction, thereby converting 5'-substituted hydantoin to the desired D-amino acids.

SUMMARY OF THE INVENTION

The present invention provides a novel D-hydantoinase gene cloned from a thermophilic *Bacillus circulans* and an expression vector to largely express D-hydantoinase in a host. In addition, the present invention discloses the optimal conditions (i.e. divalent ions, pH, temperature) of enzyme activity for conversion of 5'-substituted hydantoin to the corresponding N-carbamoyl-D- and/or -L-α/β-D-amino acids.

It is therefore a primary object of the present invention to provide an isolated nucleic acid molecule. This molecule encodes for a protein consisting of the amino acid sequence set forth in SEQ ID NO:1, wherein the protein has D-hydantoinase activity and retains at least 50% activity after incubation at 50° C. for 30 days.

Another object of the present invention is to provide a recombinant vector, which comprises the isolated nucleic acid molecule set forth above and a regulatory sequence.

Still another object of the present invention is to provide a thermostable D-hydantoinase, wherein the amino acid sequence of the D-hydantoinase is set forth in SEQ ID NO:1.

Yet another object of the present invention is to provide a method for preparing a D-amino acid, comprising reacting a 5'-substituted hydantoin with the thermostable D-hydantoinase of the present invention at a pH of 5 to 10 and at a temperature between 30° C. and 90° C.

Yet still another object of the present invention is to provide a method for the expression of a thermostable D-hydantoinase in a host cell, comprising (a) introducing the above recombinant vector into the host cell; and (b) culturing the transformed host cell under conditions sufficient to express the thermostable D-hydantoinase. The method can further comprise a step of purifying and recovering the resulting thermostable D-hydantoinase for the large production of thermostable D-hydantoinase of the present invention.

BRIEF DESCRIPTION OF THE DRAWINGS

The present invention will be more fully understood and further advantages will become apparent when reference is made to the following description of the invention and the accompanying drawings in which:

FIG. 3 is a diagram showing the construct of (A) pQE-bcidht vector, and (B) pET-bcidht vector;

FIG. 4 is a diagram showing the nucleotide sequence of the thermostable D-hydantoinase with enzyme activity of the present invention (SEQ ID NO:2), and the deduced amino acid sequence thereof (SEQ ID NO:1);

DETAILED DESCRIPTION OF THE INVENTION

Figure 1:
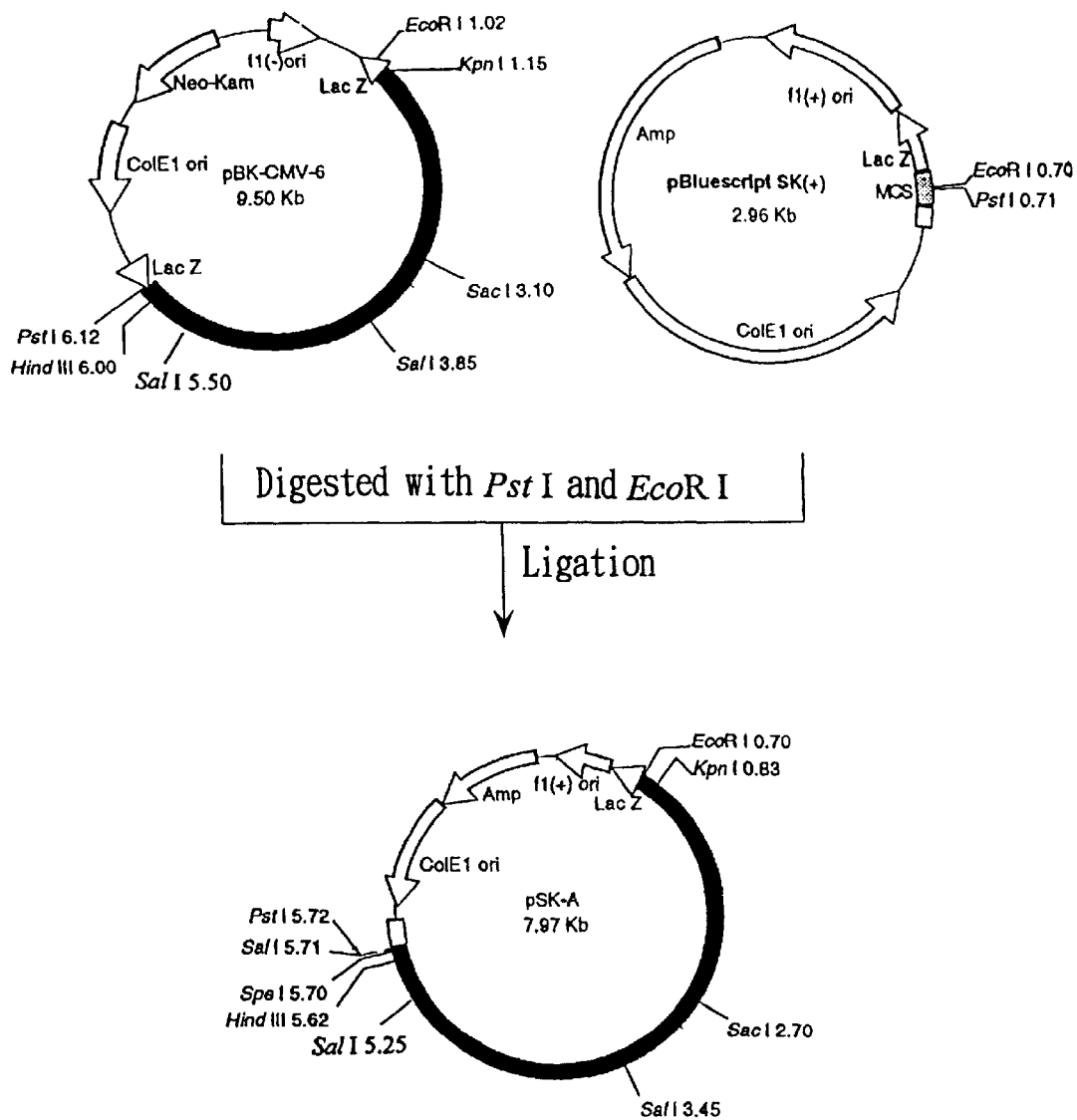
FIG. 1 is a schematic diagram showing the construct of pSK-A vector.

In accordance with the present invention, there is provided a novel D-hydantoinase gene isolated from a thermophilic *Bacillus circulans*, which the gene encodes for a novel thermostable D-hydantoinase. In one preferred embodiment, the enzyme retains at least 50% D-hydantoinase activity after incubation at 50° C. for 30 days. The isolated nucleic acid molecule comprises at least the nucleotide sequence as set forth in SEQ ID NO:2 or the complementary sequence thereof. Those skilled in the art belonging to molecular biology will appreciate that the DNA sequence can be slightly modified using any method known to this art. For example, degenerate codon can be used to replace the corresponding sites without changing the encoded amino acid sequence. Furthermore, additional codons can be added to the 3'- or 5'-end of the DNA sequence or inserted in the DNA sequence, but the activity of the resulting enzyme is only slightly affected, if at all. Genetic engineering methods such as addition, deletion, substitution, etc., are well-known to those skilled in this art and can be seen in Sambrook, et al., Molecular Cloning, A Laboratory Manual, Cold Spring Harbor Laboratory Press, New York, 1989. Those modified sequences are all within the scope of the present invention.

The present invention also provides a recombinant vector comprising the isolated nucleic acid molecule as set forth above and a regulatory sequence. The regulatory sequence used herein can include, for example, plasmid replication origin sequence, selection marker, transcriptional promoter, etc. Suitable promoter sequences for the present invention include, for example, cytomegalovirus (CMV) promoter, simian virus 40 (SV40) early promoter, Rous sarcoma virus (RSV) promoter, etc.

According to the isolated nucleic acid molecule of the present invention, one skilled in this art can express the desired gene product (i.e. D-hydantoinase) in any appropriate manner, with which the D-hydantoinase possesses the amino acid sequence as set forth in SEQ ID NO:1.

The present invention further provides a method for preparing a D-amino acid, comprising reacting a 5'-substituted hydantoin with the thermostable D-hydantoinase of the present invention under suitable conditions, for example, at a pH from 5 to 10 and at a temperature from 30° C. to 90° C. The form of thermostable D-hydantoinase used herein can include purified D-hydantoinase, bacteria containing the recombinant vector set forth above or the crude extracts thereof. Suitable substrates (i.e. 5'-substituted hydantoin) include, but are not limited to, hydantoin, dihydrouracil, D,L-p-hydroxyphenylhydantoin or D,L-homophenylalanyl-hydantoin. As a result, the conversion of 5'-substituted hydantoin to the corresponding N-carbamoyl-D- and/or -L-α/β-D-amino acids can be achieved using the thermostable D-hydantoinase of the present invention.

The preparation method set forth above further comprises addition of divalent metal ions to enhance the enzyme activity of the present invention. Suitable examples of divalent metal ions include, for example, cobalt ($Co^{2+}$), manganese ($Mn^{2+}$), or nickel ($Ni^{2+}$)

The present invention also provides a method for expression of a thermostable D-hydantoinase in a host cell, comprising introducing the above recombinant vector into the host cell, and then culturing the transformed host cell under conditions sufficient to express the thermostable D-hydantoinase. The method can further comprise a step of purifying and recovering the resulting thermostable D-hydantoinase for the large production of thermostable D-hydantoinase of the present invention.

The host cell used herein is not limited, and can be varied according to the cloned promoter sequence or the industrial application. Such host cells can include prokaryotic cells (e.g. *E. coli* or *Bacillus circulans*) or eukaryotic cells (e.g. yeast cell).

The genetic engineering methods used herein, such as DNA modification, cloning and isolation of recombinant vectors, expression and purification of proteins, etc., are well-known to those skilled in this art and can be seen in Ausubel, F. M. et al., Current Protocols in Molecular Biology, New York, 1992; Sambrook et al., supra; and Davis, L. G., Methods in Molecular Biology, Elsevier, Amsterdam, NL, 1986.

Without intending to limit it in any manner, the present invention will be further illustrated by the following examples.

EXAMPLE

Example 1

Cloning of D-hydantoinase Gene (1) Design of probes for D-hydantoinase gene The amino acid sequences of the known D-hydantoinases were collected from database, and aligned using GCG program. The DNA sequences with high homology were designed as primers, with the following designated names and sequences:

ADHT-1: 5'-TTCCAGGCGGCATCGACCCGCA-3' (SEQ ID NO:3)

ADHT-2: 5'-GGCGCGGCCGGCCGCTTCACCTTC-3' (SEQ ID NO:4)

ADHT-6: 5'-CCATTCTCCGCATGCACCCATG-3' (SEQ ID NO:5)

Two DNA fragments, 510 bp and 400 bp in length were amplified from chromosomal DNA of *Bacillus circulans* by polymerase chain reaction (PCR). The PCR amplification consisted of 0.075 units pfu Turbo™ DNA polymerase (STRTAGENE®, La Jalla, Calif. and 1 µM of primers pair of ADH-1 and ADH-2, and another pair of ADH-1 and ADH-6, respectively. PCR was carried out in 4 stages: (1) 94° C. for 3 min; (2) 94° C. for 1.5 min, 65° C. for 2 min, 72° C. for 2 min, 25 cycles; (3) 94° C. for 1.5 min, 65° C. for 1 min, 72° C. for 3 min, 1 cycle; and (4) hold at 4° C. The PCR products were sequenced and compared with D-hydantoinases from other organisms in their amino acid sequences. The D-hydantoinase of the present invention showed about 45%–70% identity in amino acid sequence with other D-hydantoinases. The PCR fragment with 510 bp in length was used as a probe for subsequent cloning of *Bacillus circulans* D-hydantoinase.

(2) Cloning of D-hydantoinase Gene

The genomic DNA library from *Bacillus circulans* was hybridized with the $^{32}$P-labeled 510-bp DNA probe. The positive clones were assayed for activities using a selective medium (LB medium containing 1% hydantoin and 0.005% phenol red, pH 7.7). The results show the medium turning from red to bright yellow in color only in the group of pBK-CMV-6 bearing *E. coli* XLORL, indicating that this clone possesses the enzyme activity of D-hydantoinase and contains a full-length D-hydantoinase gene which can be expressed in *E. coli*.

(3) Construction and Sequencing of the Recombinant Vectors pSK-A and pSK-B

Vector pBK-CMV-6 was digested with the restriction enzyme group of EcoRI and PstI, and with another group of PstI and XbaI. A DNA fragment about 5 kb in length was recovered, and then ligated to pSK(+) vector pre-digested with the same restriction enzymes. The resulting recombinant vectors were designated pSK-A (FIG. 1) and pSK-B (FIG. 2), respectively. Deletion reaction was carried out on both pSK-A and pSK-B vectors using exonuclease III to obtain the deleted fragments with various length. These fragments were ligated, and then transformed into *E. coli* NovaBlue. The transformed clones were selected and sequenced via T7 primer located on the vector. After analysis by DNASTAR software, one full-length D-hydantoinase gene was obtained. This D-hydantoinase gene is 1,386 bp in length, and the 461 amino acids are encoded by the open reading frame (ORF), with a molecular weight of 50,485 Da (Referring to FIG. 4). Other biochemical properties include: G+C content, 57.86%; hydrophobic amino acid content, 37%; polar amino acid content, 24%; iso-electric point (pI) 5.7; and electric charge −10.8 at pH 7.0.

Example 2

Construction of Recombinant Vector and Expression of D-hydantoinase

According to the DNA sequence of D-hydantoinase gene, the forward primer was synthesized from the origin of ORF, comprising a BamHI cleavage site. On the other hand, the reverse primer was synthesized from 100 bp downstream of stop codon, comprising a HindIII cleavage site. The D-hydantoinase gene fragments were amplified by PCR, followed by digestion with BamHI and HindIII. The treated DNA fragments were ligated into expression vectors pQE-30 and pET-21b, and designated pQE-bcidht (FIG. 3(A)) and pET-bcidht (FIG. 3(B)), respectively. The vector pQE-bcidht was transformed into *E. coli* NovaBlue to express D-hydantoinase. After culturing the transformants, 1 mM IPTG was added to induce expression when the absorbance of $OD_{600}$ reached 1.0. The induced bacteria were incubated at 28° C. for 6 hours to induce the expression of proteins.

Example 3

Recovery and Purification of D-hydantoinase

The culture broth containing the induced bacteria mentioned above was collected. After ultra-sonication, the broth was centrifuged at 13,500 rpm for 20 min. The supernatant was collected and loaded onto the resin containing 6×His tag to adsorb the soluble D-hydantoinase with 6×histidine. The recovered proteins were analyzed by SDS-PAGE, and a protein band at about 51 kDa in size was noted markedly, corresponding to the size of deduced D-hydantoinase.

Example 4

Quantification of D-hydantoinase Activity (1) Reaction pH of D-hydantoinase

The substrate D,L-p-HPH was dissolved in various pH buffers at the final concentration of 10 mM. The vector pQE-bcidht in *E. coli* NovaBlue, crude extracts thereof or the purified D-hydantoinase of the present invention, were added to each buffer containing substrate, and incubated at 50° C. for 10 min. The specific activity of the enzyme was then measured.

Figure 5:
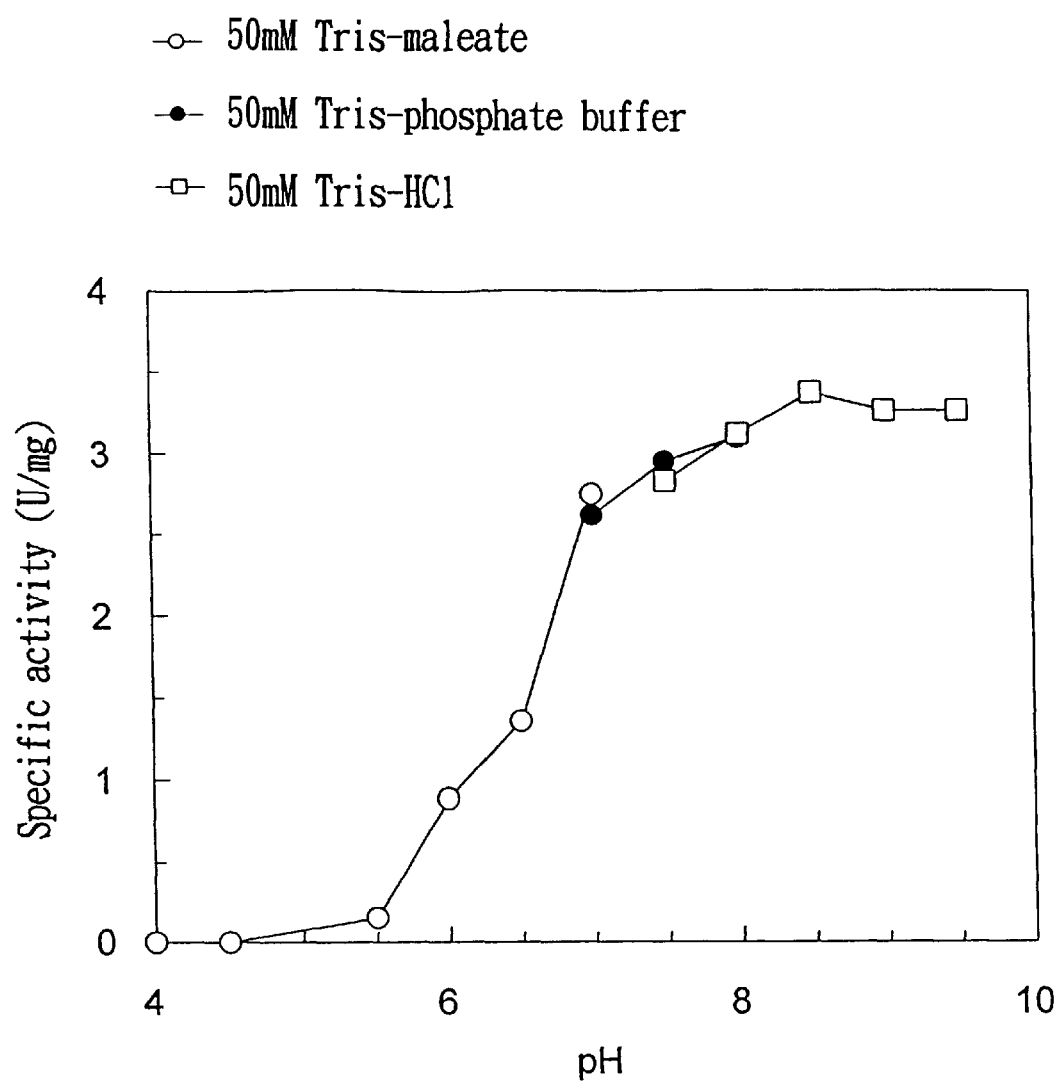
FIG. 5 is a diagram showing effects of pH on D-hydantoinase activity of the present invention.

The result is shown in FIG. 5. The lower enzyme activity is found when the solution is acidic. Further, the enzyme loses its entire activity at pH 4.0. By contrast, higher enzyme activity is found when the solution is basic, and the enzyme has the highest specific activity of 3.36 unit/mg at pH 8.5. In addition, referring to FIG. 5, enzyme activity can be found at pH levels ranging from 5 to 10. With the same pH, the specific activity of the enzyme in buffers composed of different components is not, however, identical.

(2) Reaction Temperature of D-hydantoinase

The vector pQE-bcidht in *E. coli* NovaBlue, crude extracts thereof or the purified D-hydantoinase of the present invention (containing 500 µM $Mn^{2+}$), was added to 10 mM substrate of D,L-p-HPH (dissolved in 50 mM Tris-HCl (pH 8.0)). The mixture was incubated at various temperature (30–90° C.) for 10 min. The specific activity of the enzyme was then measured.

Figure 6:
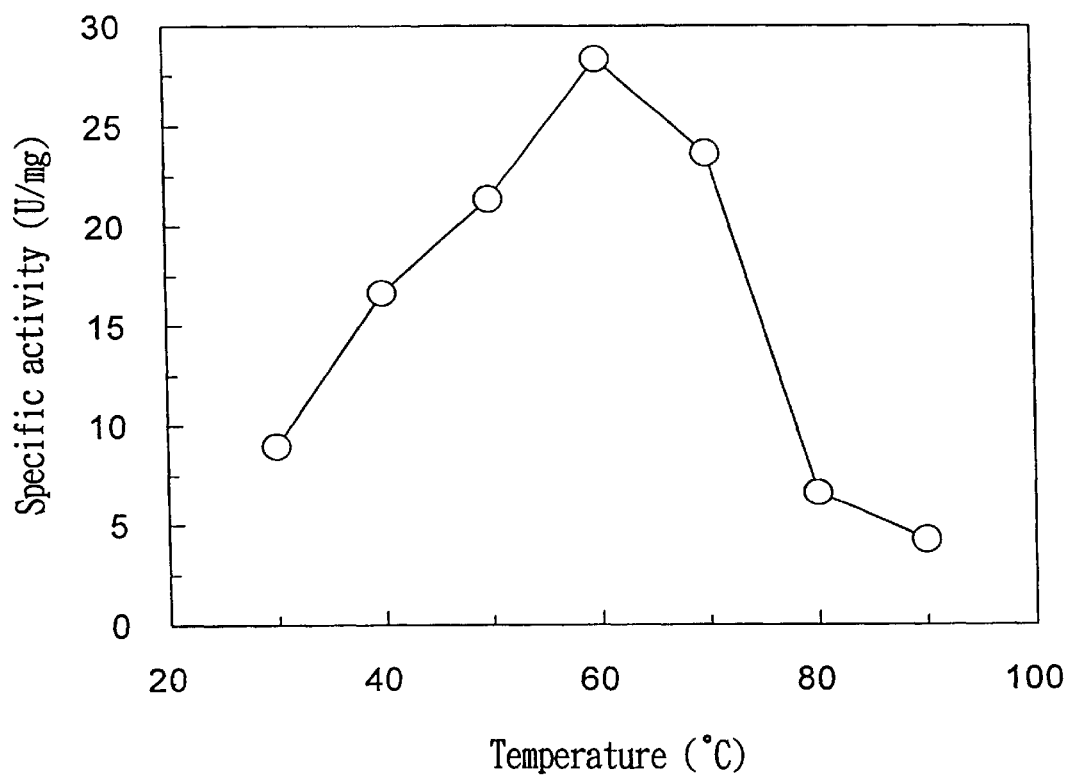
FIG. 6 is a diagram showing the effects of temperature on D-hydantoinase activity in the present invention.

The result is shown in FIG. 6. The specific activity of D-hydantoinase is only 9.0 unit/mg at 30° C. Enzyme activity increases with the elevated temperature, and the enzyme has the highest specific activity of 28.32 unit/mg at 60° C. Above 60° C., enzyme activity suddenly decreases, and with the specific activity of 4.26 unit/mg at 90° C.

(3) Thermostability of D-hydantoinase

The vector pQE-bcidht in *E. coli* NovaBlue, crude extracts thereof or the purified D-hydantoinase of the present invention (47 unit/mg; containing 500 µM $Mn^{2+}$), was incubated at 50° C. in a thermostat water bath. The specific activity of the enzyme was measured at various time intervals.

Figure 7:
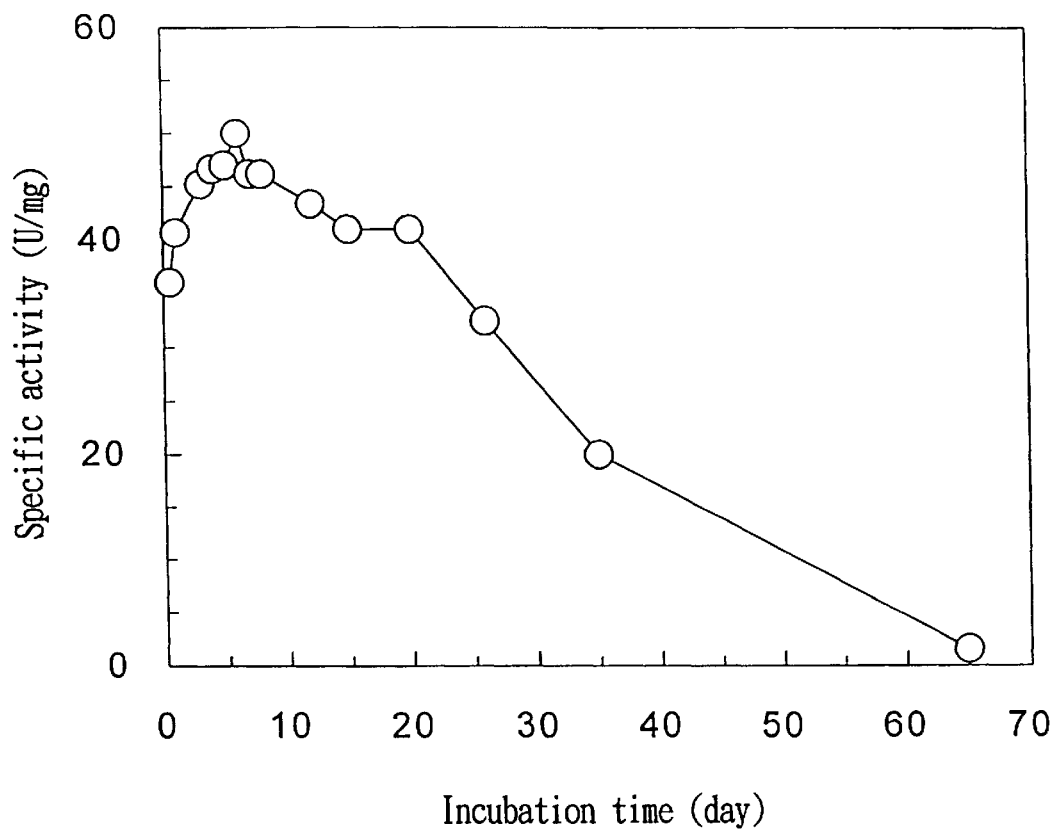
FIG. 7 is a diagram showing the thermostability test of D-hydantoinase on the present invention.

The result is shown in FIG. 7. The half-life of D-hydantoinase is about 35 days. In addition, the enzyme of the present invention retains activity after 60 days incubation at 50° C.

(4) Relationship between Metal Ions and Enzyme Activity

Various divalent metal ions (as set forth in Table 1 below) were added to the vector pQE-bcidht in *E. coli* NovaBlue, crude extracts thereof or the purified D-hydantoinase of the present invention at 500 µM concentration. After 15 minutes of incubation at room temperature, 10 mM substrate of D,L-p-HPH (dissolved in 50 mM Tris-HCl (pH 8.0)) was added. The specific activity of the enzyme was then measured.

Figure 8:
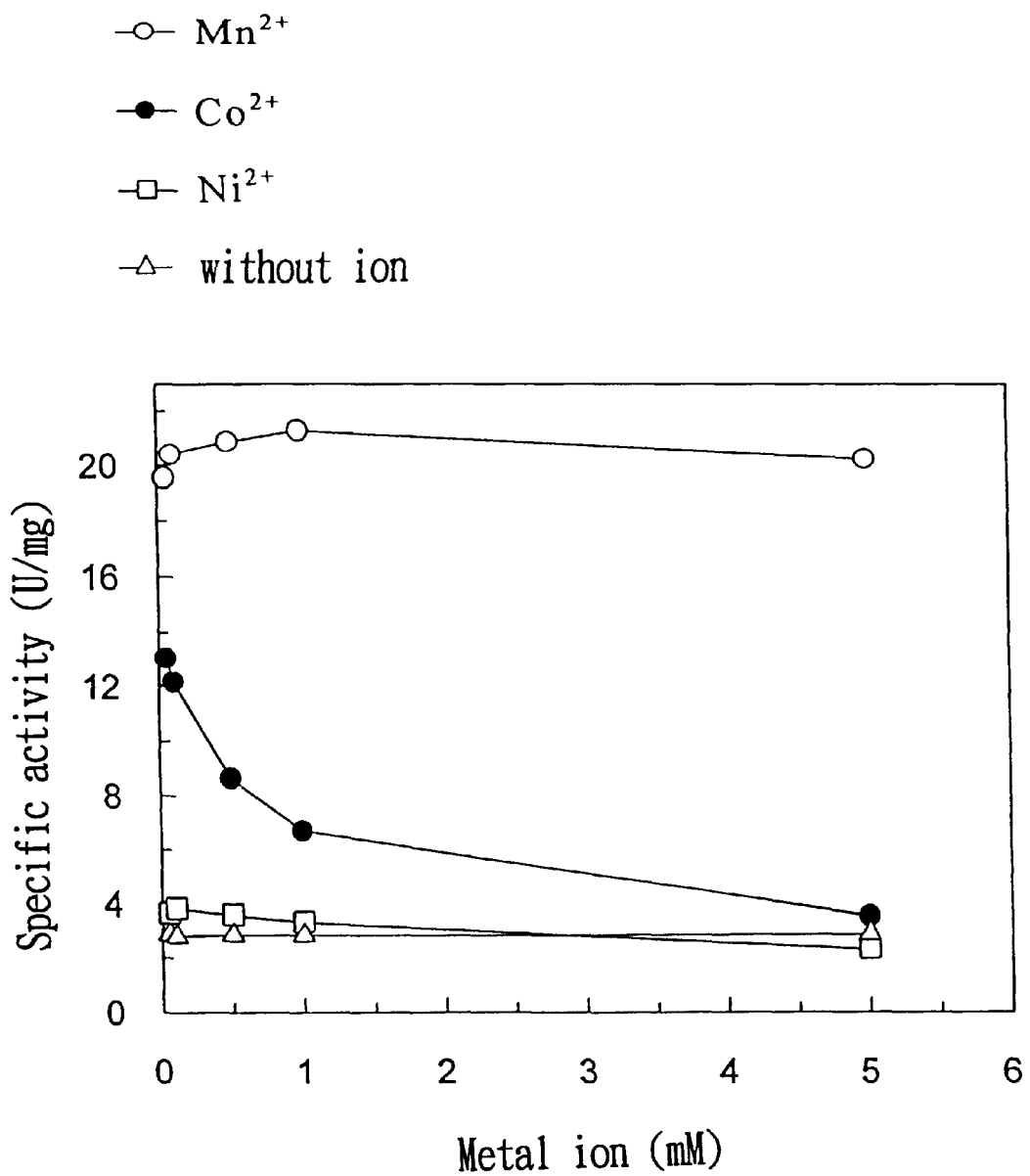
FIG. 8 is a diagram showing effects of metal ion on D-hydantoinase activity of the present invention.

The result is shown in FIG. 8. $Cu^{2+}$ and $Zn^{2+}$ inhibit D-hydantoinase activity at a level of 22% and 50%, respectively; however, $Mn^{2+}$, $Co^{2+}$ and $Ni^{2+}$ enhance the enzyme activity (Table 1). The enzyme activity markedly increases to 7.7 times original activity when the solution contains 500 μM $Mn^{2+}$. In addition, the enzyme activity increases to 4.5 and 1.3 times the original activity in the presence of 50 μM $Co^{2+}$ and 100 μM $Ni^{2+}$, respectively.

TABLE 1

Effects of metal ions on D-hydantoinase activity of the present invention

| Ion (500 μM) | Specific activity (unit/mg) | Relative activity (%)[a] |
|---|---|---|
| No | 2.88 | 100 |
| $CoCl_2$ | 7.25 | 252 |
| $CaCl_2$ | 2.53 | 88 |
| $CuCl_2$ | 2.26 | 78 |
| $FeCl_3$ | 2.52 | 87.5 |
| $FeSO_2$ | 2.52 | 87.5 |
| $MgSO_4$ | 2.69 | 94 |
| $MnCl_2$ | 22.25 | 773 |
| $NiSO_4$ | 4.00 | 139 |
| $ZnSO_4$ | 1.44 | 50 |
| $MgCl_2$ | 2.62 | 91 |

[a]Relative activity represents the activity percentage based on that of without adding ions.

(5) Effects of Chelator on D-hydantoinase Activity

The vector pQE-bcidht in *E. coli* NovaBlue, crude extracts thereof or the purified D-hydantoinase of the present invention was mixed with hydrophilic chelator, EDTA, and hydrophobic chelator, 2,6-dipicolinic acid, at 10 μM concentration, respectively. The mixture was incubated for 0–12 hours, and the enzyme activity was measured.

Figure 9:
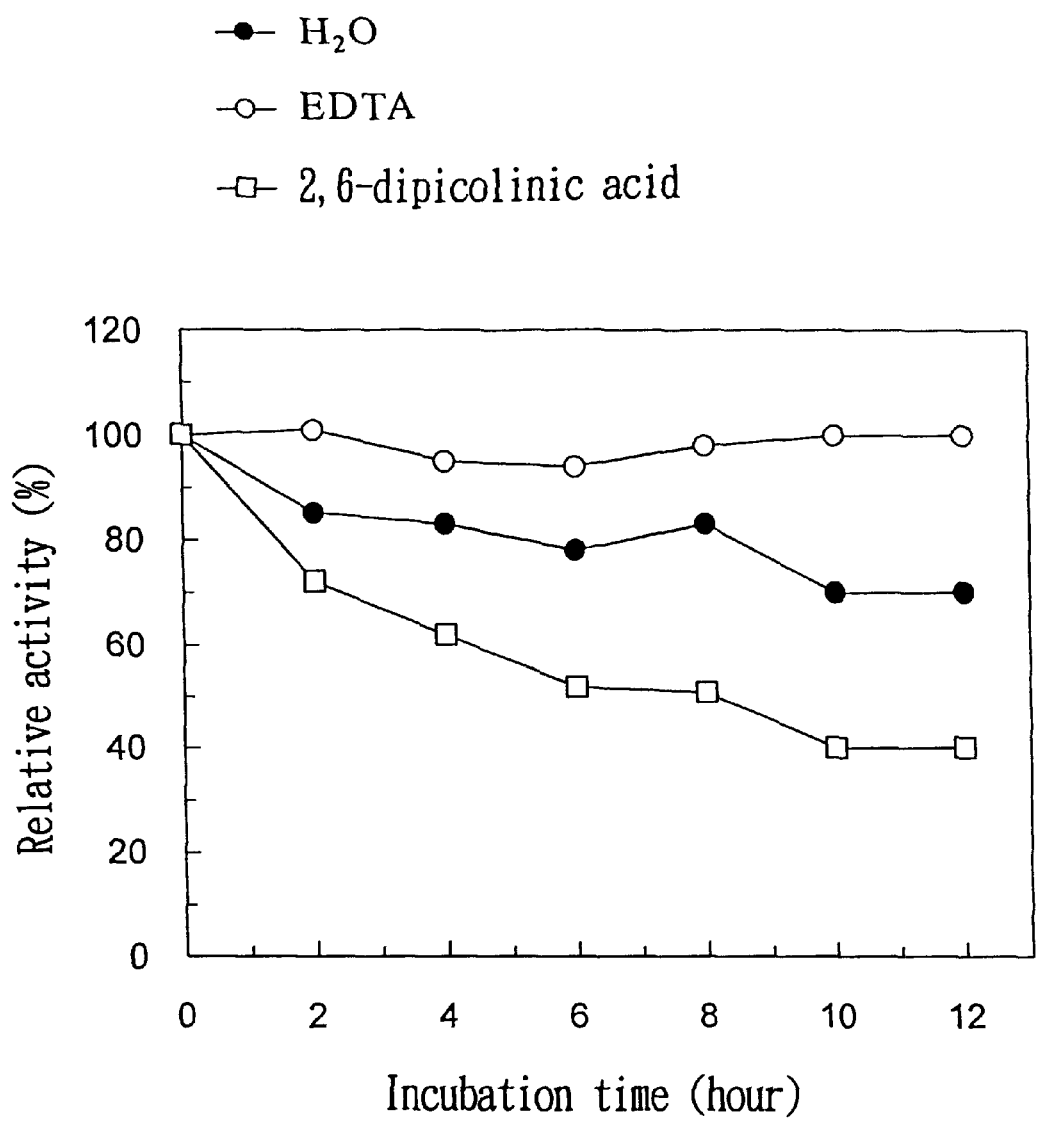
FIG. 9 is a diagram showing the effects of EDTA and 2,6-dipicolinic acid on D-hydantoinase activity in the present invention.

The result is shown in FIG. 9. The enzyme retains 70% activity after incubation with EDTA for 10 hours; whereas it retains only 40% activity after incubation with 2,6-dipicolinic acid for the same period.

(6) Effects of $H_2O_2$, NaCl, and $NH_4Cl$ on D-hydantoinase Activity

The vector pQE-bcidht in *E. coli* NovaBlue, crude extracts thereof or the purified D-hydantoinase of the present invention was incubated at 25° C. for 10 min. Afterwards, the catalase was added to the solution to remove residual $H_2O_2$, and then the enzyme activity was measured. In addition, various concentrations of NaCl and $NH_4Cl$ were added to the solution containing D-hydantoinase. The solution was incubated at room temperature for 10 min, and the enzyme activity was measured.

Figure 10:
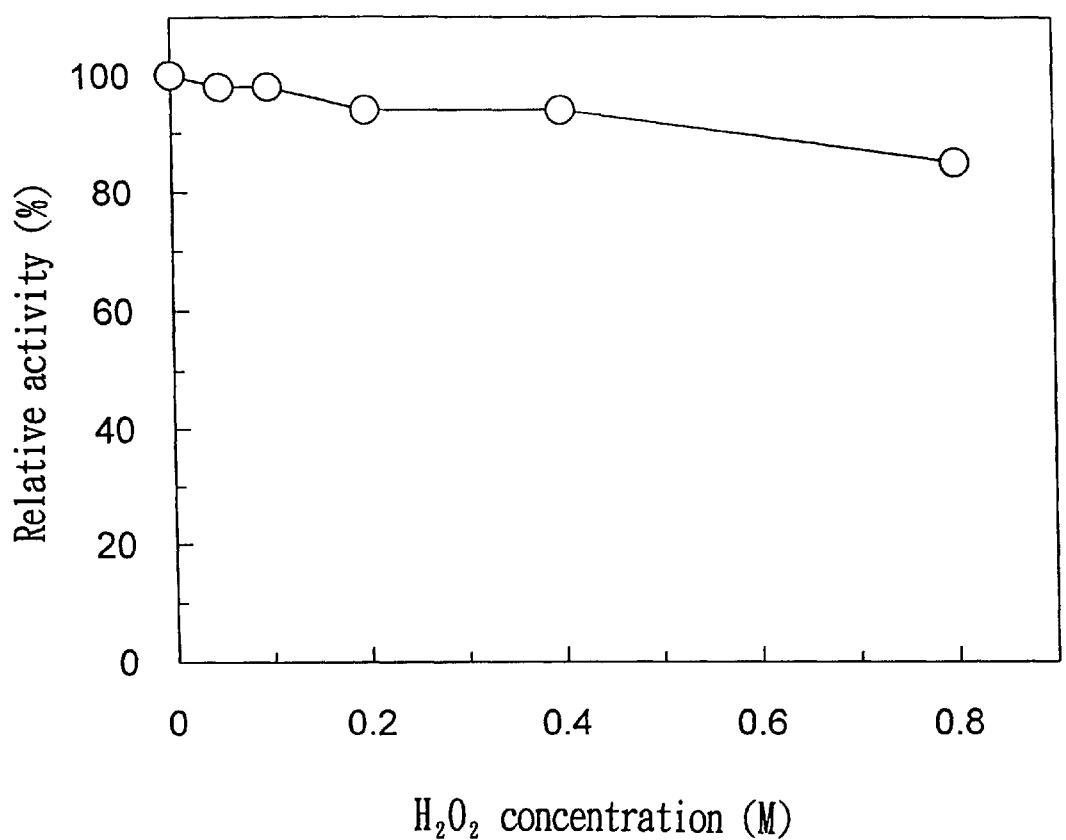
FIG. 10 is a diagram showing the effects of $H_2O_2$ on D-hydantoinase activity in the present invention.
Figure 11:
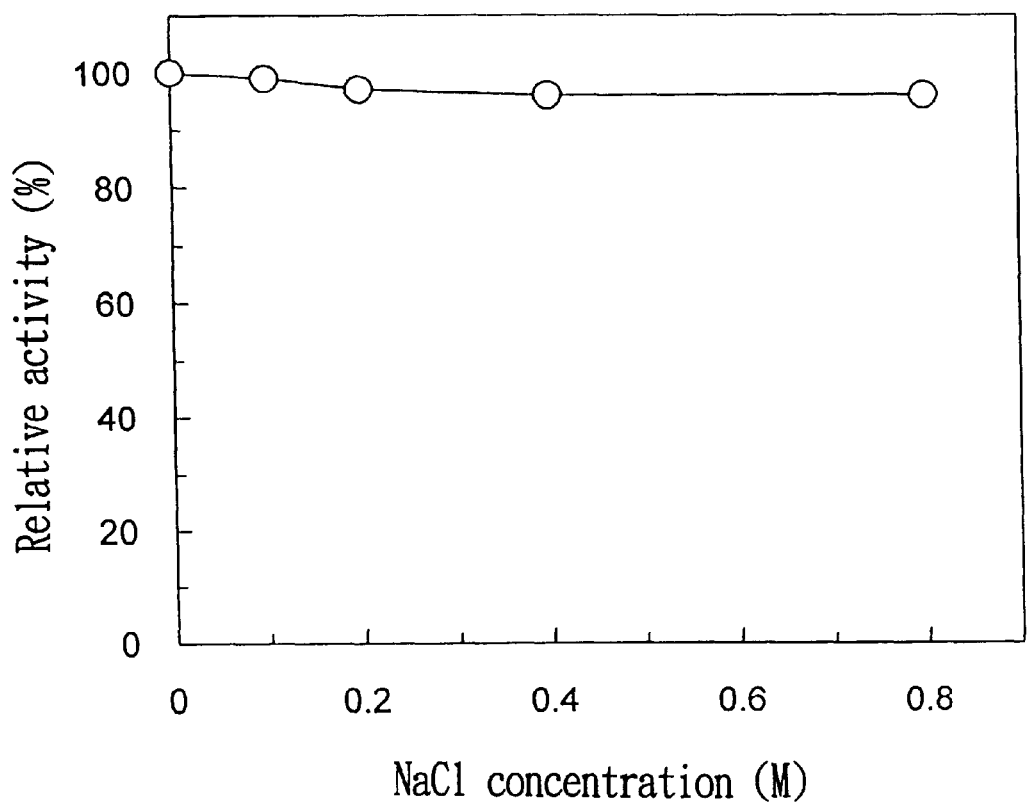
FIG. 11 is a diagram showing the effects of NaCl on D-hydantoinase activity in the present invention.
Figure 12:
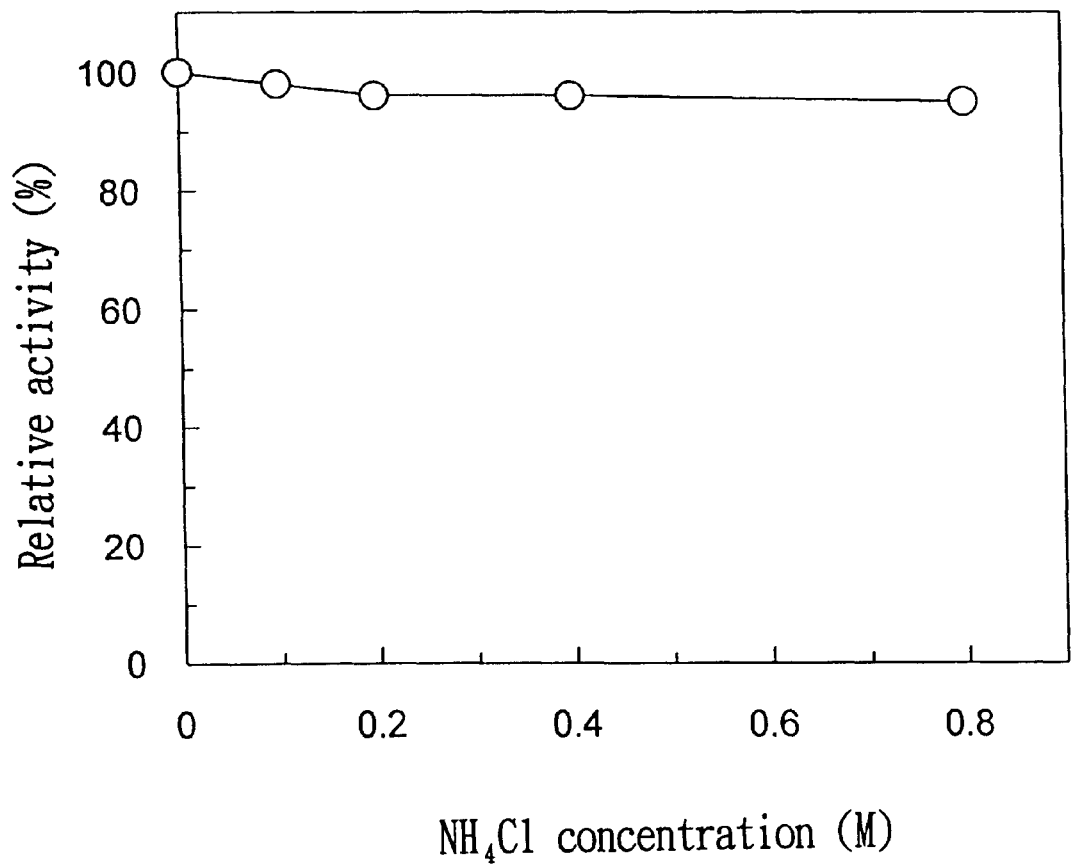
FIG. 12 is a diagram showing the effects of $NH_4Cl$ on D-hydantoinase activity on the present invention.

The results are shown in FIGS. 10–12. The enzyme retains 85% activity in the presence of 0.8 M $H_2O_2$, indicating the high resistance of D-hydantoinase in the present invention to the oxidation of $H_2O_2$. Moreover, enzyme activity is not affected even when the concentration of NaCl and $NH_4Cl$ is as high as 0.8 M, indicating the D-hydantoinase of the present invention is not inhibited by $Na^{30}$ and $NH_4^+$.

(7) Substrate Selection of D-hydantoinase 10 mM Dihydrouracil, hydantoin, D,L-p-HPH, 5-[2-(methylthio)ethyl]hydantoin, and D,L-homophenylalanyl-hydantoin were used as substrates, respectively. The vector pQE-bcidht in *E. coli* NovaBlue, crude extracts thereof or the purified D-hydantoinase of the present invention was reacted with each substrate at 50° C. for 10 min. Enzyme activity was then measured.

The result is shown in Table 2. The specific activity of D-hydantoinase for catalysis of dihydrouracil is the highest at 54 unit/mg. Further, the D-hydantoinase of the present invention is also capable of converting hydantoin, D,L-p-HPH, 5-[2-(methylthio)ethyl]-hydantoin, D,L-homophenylalanyl-hydantoin, and other 5'-substituted hydantoin to the corresponding N-carbamoyl-D- and/or -L-α/β-D-amino acids thereof.

TABLE 2

Substrate selection of D-hydantoinase of the present invention

| Substrate (10 mM) | Specific activity (unit/mg) | Relative activity (%)[a] |
|---|---|---|
| Dihydrouracil | 54.29 | 100 |
| Hydantoin | 41.43 | 76 |
| D,L-p-Hydroxyphenylhydantoin | 47.43 | 87 |
| 5-[2-(Methylthio)ethyl]-hydantoin | 21.48 | 40 |
| D,L-Homophenylalanyl-hydantoin | 45.64 | 84 |

[a]Relative activity represents the activity percentage based on that of dihydrouracil.

(8) Conditions of Converting D,L-p-HPH by D-hydantoinase

The reaction pH of D-hydantoinase is between 5 and 10. It is also found that the specific activity of the enzyme for catalysis of D,L-p-HPH can achieve the maximum level of 47 unit/mg if the enzyme is pre-mixed with $Mn^{2+}$ and incubated in an ice solution for 4 days. The substrate solubility and enzyme activity can be elevated by grinding D,L-p-HPH to powder form, dissolving the powdered substrate in 50 mM Tris-HCl (pH 8.0), followed by stirring the solution at room temperature for 2 hours. In addition, A suitable amount of DMSO can also enhance the solubility of substrate D,L-p-HPH, and elevate the conversion efficiency from D,L-p-HPH to D-p-HPG by the D-hydantoinase of the present invention.

While the invention has been particularly shown and described with the reference to the preferred embodiment thereof, it will be understood by those skilled in the art that various changes in form and details may be made without departing from the spirit and scope of the invention.

What is claimed is:

1. An isolated nucleic acid molecule which encodes a protein consisting of the amino acid sequence set forth in SEQ ID NO:1, wherein the protein has D-hydantoinase activity and retains at least 50% activity after incubation at 50° C. for 30 days.

2. The isolated nucleic acid molecule as claimed in claim 1, wherein the nucleic acid is selected from the group consisting of:
   (i) an isolated nucleic acid molecule having the nucleotide sequence of SEQ ID NO:2; and
   (ii) an isolated nucleic acid molecule complementary to SEQ ID NO:2.

3. The isolated nucleic acid molecule as claimed in claim 2, wherein the nucleic acid is isolated from *Bacillus circulans*.

4. A recombinant vector comprising the isolated nucleic acid molecule as claimed in claim 1 and a regulatory sequence.

5. The recombinant vector as claimed in claim 4, wherein the regulatory sequence comprises an operably linked promoter.

Figure 2:
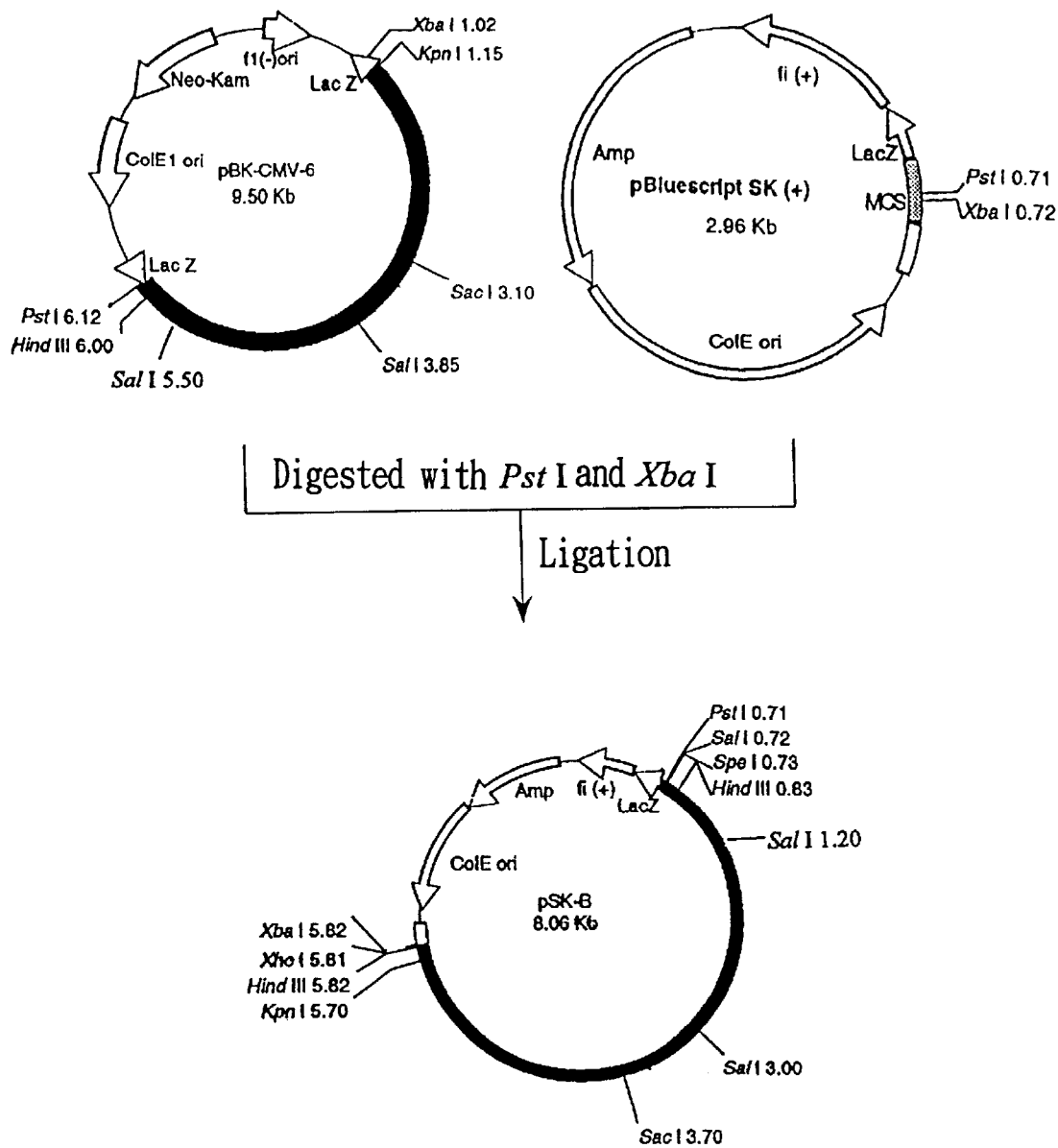
FIG. 2 is a schematic diagram showing the construct of pSK-B vector.

6. The recombinant vector as claimed in claim 5, wherein the recombinant vector is selected from the group consisting of:
   (i) pBK-CMV-6 having the construct as shown in FIG. 1, Deposit Number: PTA-2553; and
   (ii) pQE-bcidht which has the construct as shown in FIG. 3(A), Deposit Number: PTA-2554.

7. A method for expression of a thermostable D-hydantoinase in a host cell, comprising the steps of:
   (a) introducing the recombinant vector of claim 6 into said host cell; and
   (b) culturing said host cell under conditions sufficient to express the thermostable D-hydantoinase.

8. A method for producing a thermostable D-hydantoinase, comprising the steps of:
   (a) introducing the recombinant vector of claim 6 into a host cell;
   (b) culturing said host cell under conditions sufficient to produce the thermostable D-hydantoinase; and
   (c) purifying and recovering the thermostable D-hydantoinase.

9. The method as claimed in claim 8, wherein the step of purifying and recovering is performed by column chromatography.

10. The method as claimed in claim 7 or claim 8, wherein said host cell comprises a prokaryotic cell or an eukaryotic cell.

11. The method as claimed in claim 10, wherein the prokaryotic cell comprises *E.coli* cell or *Bacillus circulans* cell.

12. The method as claimed in claim 10, wherein the eukaryotic cell comprises a yeast cell.

* * * * *

SEQUENCE LISTING

<160> NUMBER OF SEQ ID NOS: 5

<210> SEQ ID NO 1
<211> LENGTH: 461
<212> TYPE: PRT
<213> ORGANISM: Bacillus circulans -continued

```
<400> SEQUENCE: 1

Met Lys Lys Trp Ile Arg Asn Gly Thr Val Thr Ala Ser Asp Thr
 1               5                  10                  15

Tyr Gln Ala Asp Val Leu Ile Asp Gly Glu Lys Val Val Ala Ile Gly
            20                  25                  30

Ser Asp Leu Gln Ala Thr Asp Ala Glu Val Ile Asp Ala Thr Gly Tyr
        35                  40                  45

Tyr Leu Leu Pro Gly Gly Ile Asp Pro His Thr His Leu Asp Met Pro
    50                  55                  60

Phe Gly Gly Thr Val Thr Ser Asp Asn Phe Phe Thr Gly Thr Lys Ala
65                  70                  75                  80

Ala Ala Phe Gly Gly Thr Thr Ser Ile Val Asp Phe Cys Leu Thr Ser
                85                  90                  95

Lys Gly Glu Ser Leu His Ser Ala Ile Ala Thr Trp His Glu Lys Ala
            100                 105                 110

Arg Gly Lys Ala Val Ile Asp Tyr Gly Phe His Leu Met Val Ser Asp
        115                 120                 125

Ala Asn Asp His Val Leu Glu Glu Leu Glu Ser Val Val Asn Asn Glu
    130                 135                 140

Gly Ile Thr Ser Leu Lys Val Phe Met Ala Tyr Lys Asn Val Leu Met
145                 150                 155                 160

Ala Asp Asp Glu Thr Leu Phe Lys Thr Leu Ile Arg Ala Lys Glu Leu
                165                 170                 175

Gly Ala Leu Val Gln Val His Ala Glu Asn Gly Asp Val Leu Asp Tyr
            180                 185                 190

Leu Thr Lys Gln Ala Leu Ala Glu Gly Asn Thr Asp Pro Ile Tyr His
        195                 200                 205

Ala Tyr Thr Arg Pro Pro Glu Ala Glu Glu Ala Thr Gly Arg Ala
    210                 215                 220

Ile Ala Leu Thr Ala Leu Ala Asp Ala Gln Leu Tyr Val Val His Val
225                 230                 235                 240

Ser Cys Ala Asp Ala Val Arg Arg Ile Ala Glu Ala Arg Glu Lys Gly
                245                 250                 255

Trp Asn Val Tyr Gly Glu Thr Cys Pro Gln Tyr Leu Val Leu Asp Ile
            260                 265                 270

Thr Ala Leu Glu Lys Pro Asp Phe Glu Gly Ala Lys Tyr Val Trp Ser
        275                 280                 285

Pro Pro Leu Arg Glu Lys Trp Asn Gln Asp Val Leu Trp Ser Ala Leu
    290                 295                 300

Lys Asn Gly Ile Leu Gln Thr Val Gly Ser Asp His Cys Pro Phe Asn
305                 310                 315                 320

Phe Ser Gly Gln Lys Glu Leu Gly Arg Arg Asp Phe Thr Lys Ile Pro
                325                 330                 335

Asn Gly Gly Pro Ile Ile Glu Asp Arg Met Thr Ile Leu Phe Ser Glu
            340                 345                 350

Gly Val Arg Lys Gly Lys Ile Ser Leu Asn Gln Phe Val Asp Ile Thr
        355                 360                 365

Ser Thr Lys Val Ala Lys Leu Phe Gly Met Phe Pro Gln Lys Gly Thr
    370                 375                 380

Ile Ala Val Gly Ser Asp Ala Asp Ile Val Leu Phe Asp Pro Thr Val
385                 390                 395                 400

Gln Arg Thr Ile Ser Val Glu Thr His His Met Asn Val Asp Tyr Asn
                405                 410                 415
```

Pro Phe Glu Gly Met Gln Val His Gly Asp V al Ile Ser Val Leu Ser
        420                 425                 430

Arg Gly Ala Phe Val Val Arg Asn Lys Gln P he Val Gly His Ala Gly
        435                 440                 445

Ala Gly Arg Tyr Val Lys Arg Ser Thr Phe A la Arg Pro
        450                 455                 460

<210> SEQ ID NO 2
<211> LENGTH: 2100
<212> TYPE: DNA
<213> ORGANISM: Bacillus circulans

<400> SEQUENCE: 2

| | | | | | |
|---|---|---|---|---|---|
| aacctgtatc | aactgcaaca | aatgccatat | cgcctgtgag | gacacttcgc a | ccaatgcat | 60 |
| tgatatcgtc | aaggacgccg | caacgggaaa | agagcggttg | gtagtgcgcg a | ggaagactg | 120 |
| cgtcggctgc | aacctgtgct | cgattgtctg | tccggtggaa | ggaacgatcg a | gatggtgga | 180 |
| gattccgacg | ggcaagccgc | cgctttcctg | gaaccagcgc | caggctgctt t | ggcaggcgg | 240 |
| gggcagttgc | gagacgtaag | ttctagggcc | gatggcatga | atgggcgca a | gcggcatag | 300 |
| catgtacgag | gaacgggatg | tctcatttat | gcacggcagg | ggaaaggagc g | aggaaggtc | 360 |
| atgaaaaaat | ggattcgcaa | cgggacggtt | gtgacggcgt | cagacacgta t | caggcagac | 420 |
| gtgctgatcg | acggcgaaaa | agtcgtcgcg | atcggctcgg | acctgcaagc a | acagatgcg | 480 |
| gaggttatcg | acgcaaccgg | gtactatttg | cttccgggcg | gcattgatcc g | cacacgcac | 540 |
| ctcgacatgc | cgtttggcgg | cacggttaca | tccgataact | ttttcacggg c | acaaaagcc | 600 |
| gccgcattcg | gcgggacgac | gagcatcgtg | gacttttgcc | tgacgagcaa a | ggggagtcg | 660 |
| ctccactccg | cgattgcgac | ctggcacgaa | aaagcgaggg | gcaaagccgt c | atcgactac | 720 |
| ggcttccacc | tgatggtgtc | cgatgccaac | gaccatgtgc | tggaagagct g | gagtcggtc | 780 |
| gtgaacaacg | aaggcattac | ttcactcaaa | gtgttcatgg | cgtacaaaaa c | gtgctgatg | 840 |
| gccgacgacg | aaactttgtt | caagacgctg | atccgcgcca | aggagctagg g | gcgttggtc | 900 |
| caagtgcacg | ccgagaacgg | ggacgtgctc | gattatttga | ccaagcaggc g | ctggccgaa | 960 |
| ggaaatacac | atccgatcta | ccacgcctac | acccgtccgc | cggaagcgga g | ggagaggcg | 1020 |
| acaggccgcg | cgattgcgct | cacggcgctc | gcggatgccc | agttgtacgt c | gtgcacgtg | 1080 |
| tcctgcgccg | acgccgttcg | ccggatcgcc | gaggcgcgcg | aaaaaggctg g | aacgtctac | 1140 |
| ggagaaacat | gtccgcaata | tttggtgctc | gatatcaccg | cgctggaaaa g | ccggacttc | 1200 |
| gaaggggcga | aatacgtctg | gtccccgccg | ctgcgggaaa | agtggaacca g | gacgtactg | 1260 |
| tggagcgcgc | tgaaaaacgg | gattttgcaa | acagttggtt | ccgaccactg t | ccgttcaac | 1320 |
| ttttccgggc | aaaaagagct | gggccgcaga | gattttacga | aaattccgaa t | gcggcccg | 1380 |
| atcattgagg | atcgcatgac | catcctcttt | tccgagggcg | tgcgcaaagg c | aaaatcagc | 1440 |
| ctgaatcaat | tcgtggacat | cacctccacc | aaagtcgcca | agctgtttgg c | atgttcccg | 1500 |
| caaaaaggca | cgattgcggt | tggctccgat | gcggacatcg | tcttgttcga c | ccgactgtg | 1560 |
| cagcggacga | tttcggtgga | gacgcaccat | atgaatgtgg | actacaaccc g | tttgaaggc | 1620 |
| atgcaggttc | acgcgacgt | catttctgtg | ctttcccgcg | gcgcgttcgt c | gtccgcaac | 1680 |
| aagcagttcg | tcggccatgc | ggggcgggc | cgctacgtga | agcggtcgac g | tttgccaga | 1740 |
| ccatagccaa | atgcaaatgc | tggggtgagg | aggagcaaga | tggcggataa a | gtgacgatc | 1800 |
| gggctgattc | aggccaaaaa | tgacgtgcac | ggcgacgagc | cggttcatct t | cacaaggaa | 1860 |

```
aaggcgatcg aaaagcatgt gaaaatggtg cgggaggctg ctggcaaagg g gcgcagatc      1920 atctgtctgc aagaaatttt ttacggccct tatttttgcg cggagcaaag c acgaaatgg     1980 tacgaagcgg cggaagaggt gccgaacggc ccgactgtgc agcagttttc c gcgctgggc     2040 aaggagctcg ggaccgtgct gatcttgccc gtgtatgaaa aggtcggcat c ggcacctac    2100

<210> SEQ ID NO 3
<211> LENGTH: 22
<212> TYPE: DNA
<213> ORGANISM: Artificial Sequence
<220> FEATURE:
<223> OTHER INFORMATION: primer for PCR

<400> SEQUENCE: 3
ttccaggcgg catcgacccg ca                                                22

<210> SEQ ID NO 4
<211> LENGTH: 24
<212> TYPE: DNA
<213> ORGANISM: Artificial Sequence
<220> FEATURE:
<223> OTHER INFORMATION: primer for PCR

<400> SEQUENCE: 4
ggcgcggccg gccgcttcac cttc                                              24

<210> SEQ ID NO 5
<211> LENGTH: 22
<212> TYPE: DNA
<213> ORGANISM: Artificial Sequence
<220> FEATURE:
<223> OTHER INFORMATION: primer for PCR

<400> SEQUENCE: 5
ccattctccg catgcaccca tg                                                22
```